(12) United States Patent
Watling et al.

(10) Patent No.: US 8,673,588 B2
(45) Date of Patent: Mar. 18, 2014

(54) COMPOSITION AND METHOD FOR HANDLING TISSUE SAMPLES

(75) Inventors: Jason Douglas Watling, Cheltenham (AU); Nick Hausler, Clayton (AU); Costa Conn, Hawthorn (AU)

(73) Assignee: Leica Biosystems Melbourne Pty Ltd, Mount Waverley Victoria (AU)

( * ) Notice: Subject to any disclaimer, the term of this patent is extended or adjusted under 35 U.S.C. 154(b) by 1059 days.

(21) Appl. No.: 12/440,235

(22) PCT Filed: Sep. 5, 2007

(86) PCT No.: PCT/AU2007/001309
§ 371 (c)(1),
(2), (4) Date: Nov. 24, 2009

(87) PCT Pub. No.: WO2008/028236
PCT Pub. Date: Mar. 13, 2008

(65) Prior Publication Data
US 2010/0075391 A1 Mar. 25, 2010

Related U.S. Application Data

(60) Provisional application No. 60/842,481, filed on Sep. 5, 2006.

(30) Foreign Application Priority Data

Sep. 5, 2006 (AU) .................. 2006904837

(51) Int. Cl.
*G01N 1/30* (2006.01)
*G01N 1/36* (2006.01)
*G01N 33/48* (2006.01)
*C12N 11/00* (2006.01)

(52) U.S. Cl.
USPC ....... 435/40.5; 435/174; 435/40.52; 435/182; 435/366

(58) Field of Classification Search
None
See application file for complete search history.

(56) References Cited

U.S. PATENT DOCUMENTS

| 4,659,700 A | 4/1987 | Jackson |
| 5,904,927 A * | 5/1999 | Amiji ............................ 424/422 |
| 6,042,874 A * | 3/2000 | Visinoni et al. .............. 427/2.11 |
| 2008/0254504 A1* | 10/2008 | Vom et al. .................. 435/40.52 |

FOREIGN PATENT DOCUMENTS

EP 0822403 B1 7/1998

OTHER PUBLICATIONS

Cocco C. et al, 2003 "Embedding media for cryomicrotomy: an applicative reappraisal", *Appl Immunohistochem Mol Morphol.* 11(3):274-280.
Fritschy W et al, 1995 "Glycol methacrylate embedding of alginate-polylysine microencapsulated pancreatic islets", *Biotech Histochem.* 70(4):188-193.
Graham E. et al, 1982 "Improved diethylene glycol distearate embedding wax", *Stain Technol.* 57(1):39-43.
Lewis P. et al, 1963 "Alginate gel; an embedding medium for facilitating the cutting and handling of frozen sections", *Stain Technol.* 38:307-310.
Mowery J. et al, 1989 "Rapid low molecular weight polyethylene glycol embedding protocol for immunocytochemistry", *J. Histochem Cytochem* 37(10):1549-1552.

* cited by examiner

*Primary Examiner* — Lisa J Hobbs
(74) *Attorney, Agent, or Firm* — Knobbe Martens Olson & Bear, LLP (57) ABSTRACT

The present invention relates to a composition and method for handling tissue samples for analysis. In particular the present invention relates to a composition and method for orientating tissue for histological and/or pathological laboratory analysis.

16 Claims, 1 Drawing Sheet

COMPOSITION AND METHOD FOR HANDLING TISSUE SAMPLES

This application is U.S. National Phase of International Application PCT/AU2007/001309, filed Sep. 5, 2007 designating the U.S., and published in English as WO 2008/028236 on Mar. 13, 2008, which claims priority to Australian Patent Application No. 2006904837 filed Sep. 5, 2006 and U.S. Provisional Application No. 60/842,481, filed Sep. 5, 2006.

FIELD OF INVENTION

The present invention relates to a composition and method for handling tissue samples for analysis. In particular the present invention relates to a composition and method for orientating tissue for histological and/or pathological laboratory analysis.

BACKGROUND OF INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

In general, tissue samples are prepared for microscopic examination using a two-stage process. The first stage usually involves processing the tissue in a tissue processor, in which the sample is processed with various fluid materials appropriate to assist in preparing the sample for the examination. In a typical tissue processing operation the tissue sample may be chemically fixed, dehydrated and cleared. During tissue processing, the tissue specimen is held loosely and individually in a cassette to segregate it from other samples. In the second stage the tissue specimen is orientated and embedded in a paraffin block ready for sectioning. This step requires skilled operators and it is time consuming to ensure that the tissue specimen is positioned correctly. In most cases, it is critical to the eventual effectiveness of the sample analysis to have the tissue sample accurately positioned and oriented in a predetermined disposition, as the sectioning of the specimen should be in appropriate planes to reveal the desired cells or structures within the tissue sample. The embedded tissue is then ready to be sectioned very thinly with a microtome, mounted on a slide, stained and finally coverslipped for microscopic examination.

A histopathology laboratory typically processes a large number of tissue samples for examination and it is important that the tissue samples be prepared as efficiently as possible. Apparatus and methods for preparing tissue samples for histological examination have progressed over the years to provide more efficiency in the preparation of tissue specimens. However, the large number of tissue samples which are prepared daily by histological laboratories require the most efficient techniques available to increase the number of samples that may be processed and to reduce the cost of such processing.

The procedures described above require the histologist to spend a large proportion of their time removing the tissue from the cassette after tissue processing and then orientating the samples in wax in their own moulds.

Furthermore, the inventors have recognised that tissue samples are generally getting smaller than in the past because biopsies, being in common use, are less invasive to the patient. The small size of tissue samples also presents additional tissue handling problems.

Whilst automation of various tissue handling procedures have improved the speed and efficiency of preparing tissue samples for analysis, there remains a need for further compositions and methods to further improve the speed and efficiency of preparing tissue samples for analysis.

In certain embodiments, the present invention may provide a composition and method that alleviates at least one disadvantage of the prior art.

SUMMARY OF INVENTION

In a first aspect the present invention provides a method of disposing a tissue sample at a supporting surface of a tissue handling device, the method comprising the steps of applying an orientating composition to the surface, wherein the composition comprises at least one organic solvent and a gelling agent and wherein the composition is substantially liquid at room temperature;

applying the tissue sample to the orientating composition such that the tissue sample is affixed relative to the surface in a predetermined orientation.

In a second aspect, the present invention provides a method of disposing a tissue sample at a supporting surface of a tissue handling device, the method comprising the steps of applying the tissue sample to the surface, applying an orientating composition to the surface such that the tissue sample is affixed relative to the surface in a predetermined orientation, wherein the composition comprises at least one organic solvent and a gelling agent and wherein the composition is substantially liquid at room temperature.

In a third aspect, the present invention provides a method of disposing a tissue sample at a supporting surface of a tissue handling device, the method comprising the steps of priming the surface of the tissue handling device with a priming agent, applying an orientating composition to the surface, wherein the composition comprises at least one organic solvent and a gelling agent and wherein the composition is substantially liquid at room temperature, applying the tissue sample to the surface such that the tissue sample is affixed relative to the surface in a predetermined orientation.

In one embodiment, the method of disposing a tissue sample at a supporting surface according to any one of the first to third aspects of the invention further comprises applying at least one step of a tissue handling procedure to the affixed tissue sample, such as chemically fixing, dehydrating or clearing. Advantageously, the at least one step may be performed prior to or subsequent to disposing the tissue sample.

In some embodiments, the organic solvent is selected from the group comprising ethanediol, 1,3-propanediol, glycerol, 1.2 propanediol, 1.2 butanediol, 1.3 butanediol, 1.4 butanediol, polyethylene glycols such as diethylene glycol, triethylene glycol, alcohols such as methanol, ethanol, dimethylformamide, formamide, dimethylsulfoxide (DMSO) or combinations thereof.

In some embodiments, the gelling agent is a carbohydrate based polymer selected from the group comprising agarose, including agarose derivatives and modified agarose such as low melt agaroses, hydroxyethylagaroses and low molecular weight agaroses, agar, alginates, dextran, mannan, pectin, Ghatti gum and cellulose, including hydroxypropylcellulose, or combinations thereof.

In one embodiment, the present invention provides a method according to any one of the first to third aspects of the invention, further comprising the step of exposing the orientating composition to a further liquid.

The further liquid may be an aqueous or non-aqueous liquid. In one embodiment, the further liquid is an aqueous liquid.

In one embodiment, the orientation composition for use in the present invention comprises a di or poly amine.

In one embodiment, the di or poly amine is selected from the group consisting of chitosan, chitosan derivative, partly hydrolysed chitin, polylysine, polyornithine, JEFFAMINE D or ED series, α,ω-diamines (e.g. 1,2-ethylenediamine, 1,3-diaminopropane, 1,4-diaminobutane, 1,8-diaminooctane), 4,4'-diaminodicyclohexylmethane, 2,2-Bis(4-aminocyclohexyl)propane or a combination thereof.

In a further embodiment the poly amine is chitosan or a chitosan derivative and has a 5%-95% degree of acetylation.

In an embodiment of the invention, when the orientation composition comprises a di or poly amine, the composition substantially gels when exposed to an aldehyde.

In one embodiment the aldehyde is selected from the group consisting of formaldehyde, acetaldehyde and glutaraldehyde or a combination thereof.

In a further embodiment, the orientation composition comprises a cross-linking agent.

In one embodiment, the cross-linking agent is selected from the group consisting of hydroxybenzenes such as resorcinol, 1,3,5-trihydroxybenzene, phenol, cresols, xylenols, other substituted phenols (e.g. 4-tert-butylphenol, 4-hydroxybiphenyl, 4-nonylphenol, 4-cyclohexylphenol and 4-dodecylphenol, bisphenol A) and phenoxyacetic acids and their esters or combinations thereof.

In a fourth aspect, the present invention provides an orientating composition for supporting a tissue sample in a predetermined orientation relative to a supporting surface of a tissue handling device wherein the composition comprises at least one organic solvent, a gelling agent and a di or poly amine.

In an embodiment, the organic solvent is selected from the group comprising ethanediol, 1,3-propanediol, glycerol, 1.2 propanediol, 1.2 butanediol, 1.3 butanediol, 1.4 butanediol, polyethylene glycols, alcohols, dimethylformamide, formamide, dimethylsulfoxide or combinations thereof.

In one embodiment, the gelling agent is selected from the group comprising agarose, agarose derivatives, modified agarose, low melt agarose, hydroxyethylagarose, low molecular weight agarose, agar, alginates, dextran, mannan, pectin, Ghatti gum and cellulose including hydroxypropylcellulose, or combinations thereof.

In one embodiment, the di or poly amine is selected from the group consisting of chitosan, chitosan derivative, partly hydrolysed chitin, polylysine, polyornithine, JEFFAMINE D or ED series, α,ω-diamines (e.g. 1,2-ethylenediamine, 1,3-diaminopropane, 1,4-diaminobutane, 1,8-diaminooctane), 4,4'-diaminodicyclohexylmethane, 2,2-Bis(4-aminocyclohexyl)propane or a combination thereof.

In a further embodiment the poly amine is a chitosan or chitosan derivative and has a 5%-95% degree of acetylation.

In one embodiment, the orientation composition further comprises a cross linking agent.

In one embodiment, the cross-linking agent is selected from the group consisting of hydroxybenzenes such as resorcinol, 1,3,5-trihydroxybenzene, phenol, cresols, xylenols, other substituted phenols (e.g. 4-tert-butylphenol, 4-hydroxybiphenyl, 4-nonylphenol, 4-cyclohexylphenol and 4-dodecylphenol, bisphenol A) and phenoxyacetic acids and their esters or combinations thereof.

In another embodiment the orientating composition further comprises urea, urea derivative or a combination thereof.

In use, the orientation composition substantially gels when exposed to an aldehyde.

In one embodiment the aldehyde is selected from the group consisting of formaldehyde, acetaldehyde and glutaraldehyde or a combination thereof.

Advantageously, in some embodiments, the orientating composition interacts chemically or mechanically with the surface of the tissue handling device.

Other aspects and preferred features are disclosed in the specification and/or defined in the appended claims, forming a part of the description of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Further disclosure, objects, advantages and aspects of the present application may be better understood by those skilled in the relevant art by reference to the following description of preferred embodiments taken in conjunction with the accompanying drawings, which are given by way of illustration only, and thus are not limiting to the scope of the present invention, and in which.

DETAILED DESCRIPTION

The present invention provides a composition and method that allows the user to orientate a tissue sample at the grossing stage, so that the tissue advantageously requires no further human intervention throughout the processing and embedding step.

In a first aspect the present invention provides a method of disposing a tissue sample at a supporting surface of a tissue handling device, the method comprising the steps of applying an orientating composition to the surface, wherein the composition comprises at least one organic solvent and a gelling agent and wherein the composition is substantially liquid at room temperature;
applying the tissue sample to the orientating composition such that the tissue sample is affixed relative to the surface in a predetermined orientation.

In a second aspect, the present invention provides a method of disposing a tissue sample at a supporting surface of a tissue handling device, the method comprising the steps of applying the tissue sample to the surface, applying an orientating composition to the surface such that the tissue sample is affixed relative to the surface in a predetermined orientation, wherein the composition comprises at least one organic solvent and a gelling agent and wherein the composition is substantially liquid at room temperature.

In a third aspect, the present invention provides a method of disposing a tissue sample at a supporting surface of a tissue handling device, the method comprising the steps of priming the surface of the tissue handling device with a priming agent, applying an orientating composition to the surface, wherein the composition comprises at least one organic solvent and a gelling agent and wherein the composition is substantially liquid at room temperature, applying the tissue sample to the surface such that the tissue sample is affixed relative to the surface in a predetermined orientation.

In one embodiment, the tissue is applied to the surface prior to applying the orientating composition.

In one embodiment, the surface of the substrate is pre-treated, primed or both pre-treated and primed before use.

In some embodiments, the primer may advantageously be selected from the group consisting of cyanoacrylate adhesives, LOCTITE 770, PERMABOND SP11, BONDIT B-45 and B-45TH or combinations thereof.

In a preferred embodiment, the method of disposing a tissue sample at a supporting surface according to any one of the first to third aspects of the invention further comprises applying at least one step of a tissue handling procedure to the affixed tissue sample, such as chemically fixing, dehydrating or clearing. In further embodiments, the at least one step is performed after disposing the tissue sample.

In some embodiments, the gelling agent is a carbohydrate based polymer selected from the group comprising agarose, including agarose derivatives and modified agarose such as low melt agaroses, hydroxyethylagaroses and low molecular weight agaroses, agar, alginates, dextran, mannan, pectin, Ghatti gum and cellulose, including hydroxypropylcellulose, or combinations thereof.

Carbohydrate polymers have a high gel strength at relatively low solids content. This allows for compositions, based upon these polymers, to possess suitable mechanical strength to act as adhesives, but still offer little resistance to solvent exchange as they possess a very open and permeable structure due to their low solids. In addition carbohydrate polymers possess a strong affinity for tissue (animal and plant), which allows them to form around and adhere strongly to samples. Also, the strength of the bond of the carbohydrate polymer to the tissue handling device is sufficient that it reliably holds the tissue at the desired orientation throughout the process, but that the strength of the carbohydrate polymer's attachment to the tissue handling device is such that it still releases from the tissue handling device when the embedded wax sample is separated from the surface of the tissue handling device on which it was orientated at the completion of the embedding process. Carbohydrate polymers in general have been found to be relatively non-reactive throughout the tissue processing protocol. They also have a relatively low retention of the various dyes and stains used in the histological protocols.

The gelling agent may be present in an amount of about 0.1% (% w/v) to about 15% (% w/v). In some embodiments, the gelling agent is present in an amount of about 0.3% (% w/v) to about 10% (% w/v). In further embodiments, the gelling agent is present in an amount from about 1% (% w/v) to about 4% (% w/v).

The organic solvent may be a non-aqueous solvent selected from the group comprising ethanediol, 1,3-propanediol, glycerol, 1,2 propanediol, 1.2 butanediol, 1,3 butanediol, 1,4 butanediol, polyethylene glycols such as diethylene glycol, triethylene glycol, alcohols such as methanol, ethanol, dimethylformamide, formamide, dimethylsulfoxide or combinations thereof.

Advantageously, the orientating composition according to the present invention may further comprise an antimicrobial compound, stabilizer, preservative or combination thereof.

Substantially liquid as used herein includes orientating compositions in a suitably viscous, pliable gel or paste-like form. The substantially liquid compositions contemplated herein advantageously have a viscosity or consistency such that they may be applied via a dropper or pipette, spread (e.g. with a spreading device such as a spatula), brushed, poured, painted, coated, sprayed (e.g. aerosol) or dispensed (e.g. via a syringe pump).

The orientating composition used in accordance with the present invention is able to grip and/or mould to hold, or adhere to the tissue and is sufficient to hold the appropriate orientation of the tissue through processing when employed at room temperature.

Advantageously, in one embodiment, the tissue handling device is packaged or provided with the orientating composition, as described herein pre-applied.

Figure 1A:
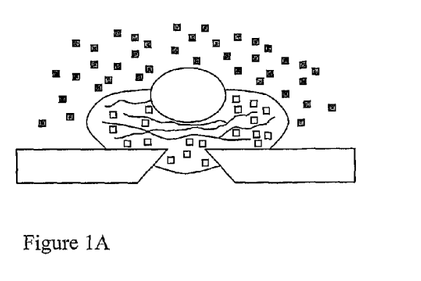
FIG. 1A to 1C shows a schematic depiction of a method of orientating a tissue sample using an orientating composition in accordance with the present invention.
Figure 1B:
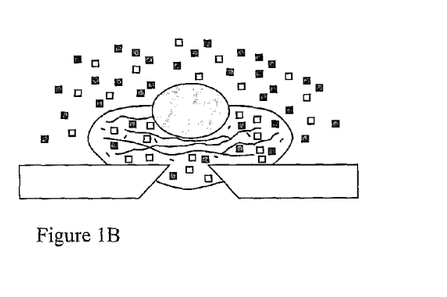
Figure 1C:
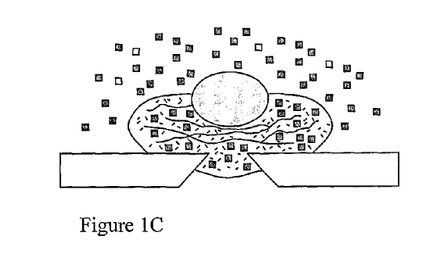

The orientating composition system as described herein the present invention is suitable for adhering tissue samples (originating from either an animal or plant) onto a tissue handling device such that the sample can be held at a predetermined orientation throughout the tissue processing and embedding process. The orientation composition is especially suitable for use in an automated tissue processing system, such as the Peloris™ Tissue Processor. The orientating composition is able to hold the sample sufficiently to enable orientation to be conducted, but to still be initially flexible enough to allow fine alignment to be conducted once the tissue is in place. The orientating composition ° is designed, primarily, such that upon coming into contact with a further liquid, such as an aqueous solution, the orientating composition develops its maximum final strength as quickly as possible, and is substantially inflexible. FIG. 1A shows an orientating composition according to a preferred embodiment of the present invention exposed to an aqueous solution (filled squares). Solvent (empty squares) is shown present in the composition. In FIG. 1B, solvent diffuses out of the composition and water diffuses into the composition and hydrogen bonding increases. In FIG. 1C, water eventually dominates and gelation occurs.

In one embodiment, the method according to any one of the first, second and third aspects of the invention further comprises exposing the orientating composition to a further aqueous liquid. Further aqueous liquid may comprise liquid, such as water or other liquid, present in the tissue sample that diffuses into the orientating composition on contact and may provide an initial tackiness to engage the tissue.

Contact of the orientating composition with further liquids, such as an aqueous solution of chemicals typically used in tissue fixation, results in substantial gelling of the orientating composition. In most cases it is expected that further liquids in which the carbohydrate polymer is to be immersed are aqueous based. As, after orientation of the tissue, the orientating composition is generally exposed to an aqueous environment, water diffuses from the aqueous solution into the orientating composition, and solvent diffuses out of the orientating composition, which results in the carbohydrate polymer matrix eventually containing a sufficient water to gel ratio to become sufficiently solid.

In one embodiment, the aqueous solution is selected from the group comprising formalin, phosphate buffered water, deionised water or combinations thereof.

The addition of a further liquid may be achieved by, for example, the use of a gas phase, such as steam for the addition of water.

By putting a degree of water back into the carbohydrate/solvent system, the quantity of water expected to be required to diffuse into the gel is lower because the gel already has a significant water content present. However, other solvents, such as non-aqueous based solvents have been successfully employed, as causing the orientating composition to gel on coming into contact with the orientating composition, and are within the scope of the present invention.

The addition of water to the carbohydrate/solvent system, in addition to allowing the tailoring of the final physical properties of the gel, also allows a range of solvents to be used that the aforementioned carbohydrates would not be suitably soluble in. Significantly higher quantities of a carbohydrate polymer, such as agarose, can be dissolved in solvents such as ethanediol if a quantity of water is added into the solvent with the carbohydrate. The quantity of water is chosen such that it allows full solubility of the desired weight percent of carbohydrate in the adhesive formulation, and sufficient viscosity for the intended application, but is below the level at which the water content is too high for the intended application.

The use of a non aqueous solvent in the orientating composition according to an embodiment of the present invention, does not allow, as water does, the establishment of sufficient tertiary structure within the orientating composition to allow the carbohydrate polymer to gel the composition—as agarose and agarose derivatives (among those mentioned) can do when water is the predominant solvent in the formulation. As a result of this, the orientating composition generated from the carbohydrate solution is substantially liquid at room temperature which aids the ease of dispensation. If a formulation of higher viscosity is desired, or of a different physical consistency is preferred, such as a paste or soft pliable gel, then such physical characteristics can be conveniently obtained within the current system by back adding an additional component, for example water, into the carbohydrate polymer/solvent system until the desired properties are obtained.

In some embodiments, water may advantageously be back added at about 0% (v/v) to about 80% (% v/v), for example, water is back added at about 10% (% v/v) to about 70% (% v/v) or, water is back added at about 25% (% v/v) to about 50% (% v/v).

The consistency of the orientation composition will typically depend upon the amount of gelling agent and the type of organic solvent selected, as well as the amount of water back added.

Typically, the back addition of about 30% (% v/v) to about 70% (% v/v) water will result in a paste or pliable gel.

The presence of water can also provide significant influence over the gelation time of the orientating composition once it is immersed in water. Without being limited by theory, the mechanism, by which this orientating composition cures, is through the exchange of the solvent within the network of the carbohydrate polymer for the solvent that the orientating composition is immersed in, is preferably in significant excess.

In a fourth aspect, the present invention provides an orientating composition for supporting a tissue sample in a predetermined orientation relative to a supporting surface of a tissue handling device wherein the composition comprises at least one organic solvent, a gelling agent and a di or poly amine.

The di or poly amine may be selected from the group consisting of chitosan, chitosan derivative, partly hydrolysed chitin, polylysine, polyornithine, JEFFAMINE D or ED series, α,ω-diamines (e.g. 1,2-ethylenediamine, 1.3-diaminopropane, 1,4-diaminobutane, 1,8-diaminooctane), 4,4'-diaminodicyclohexylmethane, 2,2-Bis(4-aminocyclohexyl) propane or a combination thereof.

In one embodiment, the poly amine is chitosan or a chitosan derivative and has a 5%-95% degree of acetylation.

The gelling agent may advantageously include a free hydroxyl group. In one embodiment, the gelling agent includes other functional groups.

In use, the orientation composition substantially gels when exposed to an aldehyde.

In one embodiment, the aldehyde is selected from the group consisting of formaldehyde, acetaldehyde and glutaraldehyde or a combination thereof.

In one embodiment, the aldehyde may be added using, for example a vapour phase, such as vapour phase formaldehyde.

Exposure of the di or poly amine to an aldehyde results in the formation of a hydrogel with an interpenetrating polymer network (IPN) structure.

In one embodiment, the orientating composition further comprises a cross-linking agent.

In certain embodiments, the cross-linking agent is selected from the group consisting of hydroxybenzenes such as resorcinol, 1,3,5-trihydroxybenzene, phenol, cresols, xylenols, other substituted phenols (e.g. 4-tert-butylphenol, 4-hydroxybiphenyl, 4-nonylphenol, 4-cyclohexylphenol and 4-dodecylphenol, bisphenol A) and phenoxyacetic acids and their esters or combinations thereof.

In a further embodiment, the orientating composition comprises urea, urea derivative or a combination thereof.

Addition of urea, urea derivative, or a combination thereof, can be used to control the final strength of the cured IPN hydrogel, allowing it to be formulated for a range of applications.

The IPN hydrogel enables the adhesion of biological tissue to polyacetal surfaces, such as those uses in tissue processing cassettes.

In some embodiments the orientating composition is a material that is porous to treating solutions commonly used in processing and tissue fixation.

A histologist may choose any suitable tissue handling device in which to position and orientate a tissue sample, such as a mould or tissue cassette.

Use of the methods and compositions of the invention allow tissue processing after orientating the tissue. After the orientating step, the tissue is ready for tissue processing, such as fixation. The fixing step may comprise applying a solution of about 10% formalin (which is typically 90% water) such that cross-links are formed in the orientating composition thereby rendering the orientating composition substantially insoluble during subsequent steps of the tissue handling procedure and thereby ensuring the tissue sample remains affixed to the surface of the tissue handling device during the subsequent steps of the tissue handling procedure but remains permeable to all the processing solutions.

In some embodiments, the orientating composition has a higher affinity for the tissue than the surface of the tissue handling device and releases easily from the bottom of the tissue handling device at the end of the embedding process. Generally, the strength of the bond of the orientating composition to the tissue handling device is sufficient that it reliably holds the tissue at the desired orientation throughout the processing, but the strength of the orientation composition's attachment to the surface of the tissue handling device is such that it still releases from the tissue handling device when the embedded wax tissue sample is removed at the completion of the embedding process.

The residual orientating composition that remains adhered to the tissue preferably cuts well during microtomy, and does not interfere with staining. Preferably, the orientating composition does not substantially stain significantly itself.

In the majority of histology laboratories, tissue samples are processed in a tissue handling device such as a cassette or mould that has come to be manufactured in accordance with at least one industry standard. One cassette is typically used per tissue sample in order to ensure samples may be uniquely identified and labelled to ensure accurate diagnosis. For diagnostic reasons samples may vary greatly in size, from samples that almost fill a cassette completely to small biopsies that may be less than 1 mm in diameter. In many laboratories today a large proportion of samples may be either biopsies or very small samples.

In accordance with preferred embodiments of the present invention, one or more tissue samples may be orientated in a tissue handling device such as a cassette, which is then processed in a tissue processor and subsequently embedded. The invention herein may provide a more efficient and faster way of preparing tissue samples for sectioning in a microtome.

The fluid materials used in tissue processing steps may comprise, for example, formaldehyde, alcohol, xylene, or other solvents.

In accordance with preferred embodiments of the present invention a tissue sample may be disposed in a pre-orientated position to a surface by method according to any one of the first to third aspects of the invention. The orientating composition may in preferred embodiments comprise a substance that provides an adhering function such that tissue may be adhered to the relevant surface.

The step of applying an orientating composition to the surface of the tissue handling device may also comprise the steps of heating the orientating composition and dispensing the heated orientating composition onto the surface of the tissue handling device.

In a preferred embodiment, a surface of the tissue handling device comprises recesses in the form of a patterned set of a locking hole or holes, slot or slots in which the orientating composition may cooperate to orientate a tissue sample in position relative to the surface of the tissue handling device. A surface of the tissue handling device may be specially designed with recesses, or be of a specific material, for example a plastic such as Acetal polyoxymethylene copolymer (POM), high-density polyethylene (HDPE) and polytetrafluoroethylene (PTFE-Teflon®-Dupont), to facilitate chemical or mechanical bonding of the orientating composition to the surface. The surface of the tissue handling device may comprise a further chemical composition adapted to cooperate with the orientating composition.

The technician may select multiple sized cassette/moulds depending on the size of tissue to be processed or embedded. A suitable tissue handling device is described in WO 2007028202. A controlled volume of orientating composition may be dispensed on to the base of a tissue handling device. The technician may then orientate the tissue sample in the tissue handling device. Alternatively, the tissue sample may be oriented first, and then the orientating composition dispensed onto the tissue and tissue handling device.

After orientating the tissue, at least one step of a tissue handling procedure may be applied to the orientated tissue sample and, in one embodiment, this comprises the fixation step of a tissue processing procedure.

In one embodiment, the orientating composition as described herein interacts chemically or mechanically with the surface of the tissue handling device. The surface of the tissue handling device may be chemically or mechanically pre-treated to facilitate adhesion of orientating composition.

Once the tissue is processed in a standard tissue processor, the user may proceed with embedding the tissue either manually or using an automated process by, for example, applying molten wax to the tissue handling device.

The histologist may then take the resultant block out of the embedding instrument ready for further procedure in a histological microtome.

The term "tissue handling procedure" is used herein to refer to any one of the abovementioned procedures that are performed in preparing tissue samples for examination.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

EXAMPLES

Example 1

Agarose Formulation

To a well stirred solution of 6-8.5 ml (A) of ethanediol, 1,2-propanediol or glycerol in a glass Round Bottom boiling Flask heated on an oil bath to between 120° C. and 140° C., 100 mg-300 mg of regular agarose, low-melt agarose or carrageen was added slowly, and the flask stoppered.

The solution was allowed to stir until clear and homogenous, indicating that all solids had dissolved (typically from 30 minutes to 3 hours). The temperature of the oil bath was then lowered to just below 100° C., and an amount of dH2O required to make the formulation B/100% solids, (i.e., if 7 mL ethanediol and 100 mg agarose are used, 3 mL of dH2O must be added to make the total volume 10 mL, and hence the solids 1% (% w/v). It is obvious that the amount of dH2O will always=10-A for 10 mL volumes, 20-A for 20 ml volumes, etc.) added via autopipette. Typically, the solution was observed to develop some cloudiness. The flask was restoppered and allowed to stir until the solution once again became clear and homogenous (typically from 15 minutes to 3 hours). The temperature of the oil bath was then lowered to around 70° C., and the contents of the flask decanted into a Falcon tube. The viscosity of the formulation was then assessed qualitatively daily until considered stable.

Example 2

Dimethylformamide as Solvent 1.5 g regular agarose was added to a well-stirred volume of 15 mL dimethylformamide held at 120° C. This was allowed to stir for 1 hour. This solution is a 10% (% w/v) regular agarose solution in 100% (% v/v) dimethylformamide.

Example 3

Dimethylformamide as Solvent 600 mg regular agarose was added to a well-stirred volume of 10 mL dimethylformamide held at 120° C. This was allowed to stir for 1 hour. This solution is a 6% (% w/v) regular agarose solution in 100% (% v/v) dimethylformamide.

Example 4

Dimethylformamide as Solvent 800 mg regular agarose was added to a well-stirred volume of 20 mL dimethylformamide held at 120° C. This was allowed to stir for 1 hour. This solution is a 4% (% w/v) regular agarose solution in 100% (% v/v) dimethylformamide.

Example 5

Dimethylformamide as Solvent 200 mg regular agarose was added to a well-stirred volume of 10 mL dimethylformamide held at 120° C. This was allowed to stir for 1 hour. This solution is a 2% (% w/v) regular agarose solution in 100% (% v/v) dimethylformamide.

Example 6

Ethanediol as Solvent 200 mg regular agarose was added to a well-stirred volume of 10 mL ethanediol held at 120° C. This was allowed to stir for 1 hour. This solution is a 2% (% w/v) regular agarose solution in 100% (% v/v) ethanediol.

Example 7

Ethanediol as Solvent 300 mg regular agarose was added to a well-stirred volume of 10 mL ethanediol held at 120° C. This was allowed to stir for 1 hour. This solution is a 3% (% w/v) regular agarose solution in 100% (% v/v) ethanediol.

Example 8

Ethanediol as Solvent 400 mg regular agarose was added to a well-stirred volume of 10 mL ethanediol held at 120° C. This was allowed to stir for 1 hour. This solution is a 4% (% w/v) regular agarose solution in 100% (% v/v) ethanediol.

Example 9

Ethanediol as Solvent 300 mg regular agarose was added to a well-stirred volume of 9.6 mL ethanediol held at 120° C. This was allowed to stir for 1 hour. The solution was cooled to just below 100° C. and then 2.4 mL of distilled water was added, and the solution stirred for a further 1 hour. This solution is a 2.5% (% w/v) regular agarose solution comprising 80% (% v/v) ethanediol and 20% (% v/v) water.

Example 10

Ethanediol as Solvent

To a well-stirred volume of 9 mL ethanediol held at 120° C. was added 200 mg regular agarose. This was allowed to stir for 1 hour. The solution was cooled to just below 100° C. and then 1 mL of distilled water was added, and the solution stirred for a further 1 hour. This solution is a 2% (% w/v) regular agarose solution comprising 90% (% v/v) ethanediol and 10% (% v/v) water.

Additional compositions with ethanediol as solvent are outlined in table 1.

TABLE 1 additional compositions with ethanediol as solvent.

|  | 1 | 2 | 3 | 4 | 5 | 6 | 7 |
|---|---|---|---|---|---|---|---|
| Agarose (mg) | 100 | 100 | 100 | 150 | 200 | 200 | 200 |
| water (ml) | 2.5 | 2.25 | 2 | 2.25 | 1.5 | 2 | 2.25 |
| % ethanediol | 75 | 77.5 | 80 | 77.5 | 85 | 80 | 77.5 |
| % agarose | 1 | 1 | 1 | 1.5 | 2 | 2 | 2 |
| Total volume (ml) | 10 | 10 | 10 | 10 | 10 | 10 | 10 |
|  | 8 | 9 | 10 | 11 | 12 | 13 | 14 |
| Agarose (mg) | 200 | 200 | 250 | 250 | 300 | 300 | 350 |
| water (ml) | 2.5 | 3 | 1.75 | 2.25 | 1.5 | 2 | 1.5 |
| % ethanediol | 75 | 70 | 82.5 | 77.5 | 85 | 80 | 85 |
| % agarose | 2 | 2 | 2.5 | 2.5 | 3 | 3 | 3.5 |
| Total volume (ml) | 10 | 10 | 10 | 10 | 10 | 10 | 10 |

Example 11

Dimethylformamide as Solvent 1.8 g low-melt (hydroxyethyl)agarose was added to a well-stirred volume of 30 mL dimethylformamide held at 140° C. This was allowed to stir for 1 hour. This solution is a 6% (% w/v) (hydroxyethyl) agarose solution in 100% (% v/v) dimethylformamide.

Example 12

Ethanediol as Solvent 100 mg low-melt (hydroxyethyl)agarose was added to a well-stirred volume of 10 mL ethanediol held at 120° C. This was allowed to stir for 1 hour. This solution is a 1% (% w/v) (hydroxyethyl) agarose solution in 100% (% v/v) ethanediol.

Example 13

Ethanediol as Solvent 150 mg low-melt (hydroxyethyl)agarose was added to a well-stirred volume of 10 mL ethanediol held at 120° C. This was allowed to stir for 1 hour. This solution is a 1.5% (% w/v) (hydroxyethyl) agarose solution in 100% (% v/v) ethanediol.

Example 14

Ethanediol as Solvent 100 mg low-melt (hydroxyethyl)agarose was added to a well-stirred volume of 8.5 mL ethanediol held at 120° C. This was allowed to stir for 1 hour. The solution was cooled to just below 100° C. and then 1.5 mL of distilled water was added, and the solution stirred for a further 1 hour. This solution is a 1% (% w/v) low-melt (hydroxyethyl) agarose solution comprising 85% (% v/v) ethanediol and 15% (% v/v) water.

Example 15

Ethanediol as Solvent 200 mg low-melt (hydroxyethyl)agarose was added to a well-stirred volume of 6.75 mL ethanediol held at 120° C. This was allowed to stir for 1 hour. The solution was cooled to just below 100° C. and then 3.25 mL of distilled water was added, and the solution stirred for a further 1 hour. This solution is a 2% (% w/v) low-melt (hydroxyethyl) agarose solution comprising 67.5% (% v/v) ethanediol and 32.5% (% v/v) water.

Additional compositions with ethanediol as solvent are outlined in table 2.

TABLE 2 additional compositions with ethanediol as solvent.

|  | 1 | 2 | 3 | 4 | 5 | 6 | 7 | 8 |
|---|---|---|---|---|---|---|---|---|
| Agarose (mg) | 100 | 100 | 100 | 100 | 100 | 150 | 150 | 150 |
| Volume water (ml) | 2 | 3 | 3.25 | 3.5 | 3.75 | 2 | 2.5 | 2.75 |
| Ethanediol (% v/v) | 80 | 70 | 67.5 | 65 | 62.5 | 80 | 75 | 72.5 |
| Agarose (% w/v) | 1 | 1 | 1 | 1 | 1 | 1.5 | 1.5 | 1.5 |
| Total volume (ml) | 10 | 10 | 10 | 10 | 10 | 10 | 10 | 10 |

|  | 9 | 10 | 11 | 12 | 13 | 14 | 15 | 16 |
|---|---|---|---|---|---|---|---|---|
| Agarose (mg) | 150 | 150 | 150 | 200 | 200 | 200 | 200 | 250 |
| Volume water (ml) | 3 | 3.25 | 3.5 | 2 | 2.5 | 2.75 | 3 | 2.25 |
| Ethanediol (% v/v) | 70 | 67.5 | 65 | 80 | 75 | 72.5 | 70 | 77.5 |
| Agarose (% w/v) | 1.5 | 1.5 | 1.5 | 2 | 2 | 2 | 2 | 2.5 |
| Total volume (ml) | 10 | 10 | 10 | 10 | 10 | 10 | 10 | 10 |

|  | 17 | 18 | 19 | 20 | 21 | 22 | 23 |
|---|---|---|---|---|---|---|---|
| Agarose (mg) | 250 | 250 | 250 | 300 | 300 | 300 | 300 |
| Volume water (ml) | 2.5 | 2.75 | 3 | 2 | 2.25 | 2.5 | 2.75 |
| Ethanediol (% v/v) | 75 | 72.5 | 70 | 80 | 77.5 | 75 | 72.5 |
| Agarose (% w/v) | 2.5 | 2.5 | 2.5 | 3 | 3 | 3 | 3 |
| Total volume (ml) | 10 | 10 | 10 | 10 | 10 | 10 | 10 |

Example 16

Glycerol as Solvent 100 mg low-melt (hydroxyethyl)agarose was added to a well-stirred volume of 8.25 mL glycerol held at 120° C. This was allowed to stir for 1 hour. The solution was cooled to just below 100° C. and then 1.75 mL of distilled water was added, and the solution stirred for a further 1 hour. This solution is a 1% (% w/v) low-melt (hydroxyethyl) agarose solution comprising 82.5% (% v/v) glycerol and 17.5% (% v/v) water.

Example 17

Glycerol as Solvent 200 mg low-melt (hydroxyethyl)agarose was added to a well-stirred volume of 6 mL glycerol held at 120° C. This was allowed to stir for 1 hour. The solution was cooled to just below 100° C. and then 4 mL of distilled water was added, and the solution stirred for a further 1 hour. This solution is a 2% (% w/v) low-melt (hydroxyethyl) agarose solution comprising 60% (% v/v) glycerol and 40% (% v/v) water.

Additional compositions with glycerol as solvent are outlined in table 3.

TABLE 3 additional compositions with glycerol as solvent.

|  | 1 | 2 | 3 | 4 | 5 | 6 | 7 |
|---|---|---|---|---|---|---|---|
| Agarose (mg) | 100 | 100 | 100 | 150 | 150 | 150 | 150 |
| Volume water (ml) | 2 | 2.25 | 2.5 | 1.75 | 2 | 2.25 | 2.5 |
| Glycerol (% v/v) | 80 | 77.5 | 75 | 82.5 | 80 | 77.5 | 75 |
| Agarose (% w/v) | 1 | 1 | 1 | 1.5 | 1.5 | 1.5 | 1.5 |
| Total volume (ml) | 10 | 10 | 10 | 10 | 10 | 10 | 10 |

|  | 8 | 9 | 10 | 11 | 12 | 13 | 14 |
|---|---|---|---|---|---|---|---|
| Agarose (mg) | 200 | 200 | 200 | 200 | 250 | 250 | 250 |
| Volume water (ml) | 1.75 | 2 | 3 | 3.5 | 1.5 | 1.75 | 2 |
| Glycerol (% v/v) | 82.5 | 80 | 70 | 65 | 85 | 82.5 | 80 |
| Agarose (% w/v) | 2 | 2 | 2 | 2 | 2.5 | 2.5 | 2.5 |
| Total volume (ml) | 10 | 10 | 10 | 10 | 10 | 10 | 10 |

|  | 15 | 16 | 17 | 18 |
|---|---|---|---|---|
| Agarose (mg) | 250 | 250 | 300 | 300 |
| Volume water (ml) | 2.5 | 3 | 1.5 | 1.75 |
| Glycerol (% v/v) | 75 | 70 | 85 | 82.5 |
| Agarose (% w/v) | 2.5 | 2.5 | 3 | 3 |
| Total volume (ml) | 10 | 10 | 10 | 10 |

Example 18

1,2-Propanediol as Solvent 100 mg low-melt (hydroxyethyl)agarose was added to a well-stirred volume of 6 mL 1,2-propanediol held at 120° C. This was allowed to stir for 1 hour. The solution was cooled to just below 100° C. and then 4 mL of distilled water was added, and the solution stirred for a further 1 hour. This solution is a 1% (% w/v) low-melt (hydroxyethyl) agarose solution comprising 60% (% v/v) 1,2-propanediol and 40% (% v/v) water.

Example 19

1,2-Propanediol as Solvent 200 mg low-melt (hydroxyethyl)agarose was added to a well-stirred volume of 7.5 mL 1,2-propanediol held at 120° C. This was allowed to stir for 1 hour. The solution was cooled to just below 100° C. and then 2.5 mL of distilled water was added, and the solution stirred for a further 1 hour. This solution is a 2% (% w/v) low-melt (hydroxyethyl) agarose solution comprising 75% (% v/v) 1,2-propanediol and 25% (% v/v) water.

Additional compositions with 1,2 propanediol as solvent are outlined in Table 4.

TABLE 4 additional compositions with 1,2 propanediol as solvent.

|  | 1 | 2 | 3 | 4 | 5 | 6 | 7 | 8 | 9 | 10 |
|---|---|---|---|---|---|---|---|---|---|---|
| Agarose (mg) | 100 | 150 | 150 | 200 | 200 | 250 | 250 | 250 | 250 | 300 |
| Volume water (ml) | 3.5 | 3 | 3.5 | 3 | 3.5 | 2 | 2.5 | 3 | 3.5 | 3 |
| 1,2 propanediol (% v/v) | 65 | 70 | 65 | 70 | 65 | 80 | 75 | 70 | 65 | 70 |
| Agarose (% w/v) | 1 | 1.5 | 1.5 | 2 | 2 | 2.5 | 2.5 | 2.5 | 2.5 | 3 |
| Total volume (ml) | 10 | 10 | 10 | 10 | 10 | 10 | 10 | 10 | 10 | 10 |

Example 20

Dimethylformamide and/or Dimethylsulfoxide as Solvent

Agarose or low melt agarose at about 0.3% (% w/v) to about 10% (% w/v), was added to dimethylformamide and/or dimethylsulfoxide, and water back added at about 30% (% v/v) to about 70% (% v/v). The resultant composition was typically a paste or pliable gel at room temperature.

Example 21

Ethanediol as Solvent

Agarose or low melt agarose at about 0.3% (% w/v) to about 5% (% w/v), was added to ethanediol, and water back added at about 20% (% v/v) to about 30% (% v/v). The resultant composition was typically a paste or pliable gel at room temperature.

Example 22

Glycerol as Solvent

Agarose or low melt agarose at about 0.3% (% w/v) to about 5% (% w/v), was added to glycerol, and water back added at about 15% (% v/v) to about 30% (% v/v). The resultant composition was typically a paste or pliable gel at room temperature.

Example 23

1,2-Propanediol as Solvent

Agarose or low melt agarose at about 0.3% (% w/v) to about 5% (% w/v), was added to 1,2-propanediol, and water back added at about 20% (% v/v) to about 60% (% v/v). The resultant composition was typically a paste or pliable gel at room temperature.

Example 24

Hydrogel Formulation

In the hydrogel formulation, the orientating composition comprises chitosan and a cross-linking agent.

The addition of chitosan and a cross-linking agent results in the formation of a hydrogel with an interpenetrating polymer network (IPN) which is then dissolved in a co-solvent consisting of water and a polyol solvent. In this example, ethylene glycol or glycerol were selected as the polyol solvent.

When blended together in the appropriate proportions this forms a viscous liquid, which may be applied to the surface of a tissue cassette. A piece of biopsied tissue was then placed on this liquid and orientated, then the tissue, liquid, and substrate placed in an aqueous solution containing formaldehyde or glutaraldehyde for a period of time. Without being limited by theory, the aldehyde reacts in two ways, first it forms cross-links between adjacent molecules of the chitosan and secondly, it forms urea-aldehyde oligomers which further cross-link the chitosan to itself and to the polysaccharide. This forms an interpenetrating polymeric network. At this point the adhesive sets into a firm flexible hydrogel.

Example 25

Hydrogel Formulation with Priming

The IPN hydrogel enables the adhesion of biological tissue to polyacetal surfaces, such as those uses in tissue processing cassettes. In order to enhance adhesion, the cassette surface may first be primed with a thin layer of a cyanoacrylate adhesive, e.g. Superglue, and this allowed to dry. A small quantity, e.g. 200 µL of the hydrogel adhesive is then placed on the primed cassette and the tissue placed on top and orientated. The entire cassette is then placed into a solution of buffered formalin (4%) for a period of no less than 20 minutes. This cures the adhesive and fixes the tissue to the cassette. It is likely that the tissue adhesion is aided by the formation of hemiaminal functional groups between the di or poly amine and free amino groups (e.g. from lysine residues) present on the surface of the tissue.

Example 26

Hydrogel Preparation

Anhydrous ethylene glycol (3.62 g) was heated to 120° C. and low melt agarose (0.135 mg) added in small portions with vigorous magnetic stirring. After the agarose had all dissolved the solution was cooled to room temperature and then 1 mL of a solution of 2% acetic acid containing 20 mg urea and 40 mg crab shell-derived chitosan was added with vigorous mixing. At this point the liquid began to become viscous necessitating mechanical stirring.

Any discussion of documents, devices, acts or knowledge in this specification is included to explain the context of the invention. It should not be taken as an admission that any of the material formed part of the prior art base or the common general knowledge in the relevant art on or before the priority date of the invention disclosed herein or, any claims defined herein.

While this invention has been described in connection with specific embodiments thereof, it will be understood that it is capable of further modification(s). This application is intended to cover any variations uses or adaptations of the invention following in general, the principles of the invention and including such departures from the present disclosure as come within known or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. Various modifications and equivalent arrangements are intended to be included within the spirit and scope of the invention and appended claims. Therefore, the specific embodiments are to be understood to be illustrative of the many ways in which the principles of the present invention may be practiced.

The invention claimed is:

1. A method of disposing a tissue sample at a supporting surface of a tissue handling device, the method comprising the steps of:
    applying an orientating composition to the surface;
    applying the tissue sample to the surface or to the orientating composition, wherein the tissue sample is applied before or after the orienting composition is applied such that the tissue sample is affixed relative to the surface in a specific orientation; wherein the orientating composition comprises at least one organic solvent, a gelling agent and water, said composition being substantially liquid at room temperature; wherein the organic solvent is selected from the group consisting of ethanediol, 1,3-propanediol, glycerol, 1,2 propanediol, 1,2 butanediol, 1,3 butanediol, 1,4 butanediol, dimethylformamide, formamide, dimethylsulfoxide and a combination thereof, and the gelling agent is a carbohydrate polymer selected from the group consisting of agarose, agarose derivatives, modified agarose, low melt agarose, hydroxyethylagarose, low molecular weight agarose, cross-linked chitosan, and a combination thereof, whereby the amount of water is selected such that the orientating composition is sufficiently viscous to hold the tissue sample for orientation, yet sufficiently flexible to allow fine alignment of the tissue sample; and
    exposing the orientating composition to an aqueous environment such that the orientating composition contains sufficient water to become sufficiently solid to fix the tissue sample in the specific orientation.

2. The method according to claim 1, wherein the tissue sample is applied to the surface before applying the orientating composition to the surface such that the tissue sample is affixed relative to the surface in the specific orientation.

3. The method according to claim 1, further comprising priming the surface of the tissue handling device with a priming agent selected form the group consisting of cyanoacrylate adhesives, LOCITE 770, PERMABOND SP11, BONDIT B-45 and B-45TH and combinations thereof, before applying the orientating composition to the surface.

4. The method according to claim 1, further comprising applying at least one step of a tissue handling procedure to the affixed tissue sample.

5. The method according to claim 1 wherein the orientating composition further comprises a di or poly amine, selected from the group consisting of chitosan, partly hydrolysed chitin, polylysine, polyornithine, JEFFAMINE D or ED series, α,ω-diamines (e.g. 1,2-ethylenediamine, 1.3-diaminopropane, 1,4-diaminobutane, 1,8-diaminooctane), 4,4'-diaminodicyclohexylmethane, 2,2-Bis(4-aminocyclohexyl)propane or a combination thereof.

6. The method according to claim 5 wherein the di or poly amine has a 5%-95% degree of acetylation.

7. The method according to claim 1 wherein the orientating composition further comprises a cross-linking agent selected from the group consisting of a hydroxybenzene a phenoxyacetic acid and a combination thereof.

8. The method according to claim 1 wherein the orientating composition further comprises urea.

9. The method according to claim 1, wherein the orientating composition gels when exposed to an aqueous liquid.

10. The method according to claim 9, wherein the aqueous liquid comprises an aldehyde.

11. The method according to claim 10 wherein the aldehyde is selected from the group consisting of formaldehyde, acetaldehyde and glutaraldehyde.

12. The method according to claim 1 wherein the orientating composition is applied to the surface before applying the tissue sample to the orientating composition such that the tissue sample is affixed relative to the surface in the specific orientation.

13. The method according to claim 1 wherein the organic solvent is ethanediol.

14. The method according to claim 1 wherein the gelling agent is selected from the group consisting of agarose, agarose derivatives, modified agarose, low melt agarose, hydroxyethylagarose low molecular weight agarose, cellulose, hydroxypropylcellulose, and a combination thereof.

15. The method of claim 7, wherein the hydroxybenzene is selected from the group consisting of resorcinol, 1,3,5-trihydroxybenzene, phenol, a cresol, a xylenol, a substituted phenol, 4-tert-butylphenol, 4-hydroxybiphenyl, 4-nonylphenol, 4-cyclohexylphenol and 4-dodecylphenol bisphenol A.8.

16. The method according to claim 1, wherein the organic solvent is ethanediol and the gelling agent is agarose or low melt agarose.

* * * * *

UNITED STATES PATENT AND TRADEMARK OFFICE
CERTIFICATE OF CORRECTION

PATENT NO. : 8,673,588 B2  Page 1 of 1
APPLICATION NO. : 12/440235
DATED : March 18, 2014
INVENTOR(S) : Watling et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1324 days.

Signed and Sealed this
Twenty-ninth Day of September, 2015

Michelle K. Lee
*Director of the United States Patent and Trademark Office*